United States Patent [19]
Seman et al.

[11] Patent Number: 5,811,456
[45] Date of Patent: Sep. 22, 1998

[54] MONOAMINE OXIDASE B INHIBITORS, PROCESSES FOR THEIR PREPARATION AND USE THEREOF

[75] Inventors: Michel Seman, 7 rue Béranger, 75003 Paris; Suzanne Bernard, Paris; René Milcent, Aulnay-Sous-Bois; Catherine Paillat, Chatou, all of France

[73] Assignees: Laboratoires Mayoly Spindler, Chatou; Michel Seman, Paris, both of France

[21] Appl. No.: 676,199

[22] PCT Filed: Jan. 19, 1995

[86] PCT No.: PCT/FR95/00061

§ 371 Date: Aug. 6, 1996

§ 102(e) Date: Aug. 6, 1996

[87] PCT Pub. No.: WO95/19960

PCT Pub. Date: Jul. 27, 1995

[30] Foreign Application Priority Data

Jan. 19, 1994 [FR] France ................................ 94 00557

[51] Int. Cl.⁶ ........................ A61K 31/275; C07C 255/03
[52] U.S. Cl. ....................... 514/523; 514/486; 514/487; 514/476; 514/520; 514/521; 514/522; 514/590; 514/595; 558/391; 560/24; 560/29; 564/36; 564/56; 564/142; 564/148
[58] Field of Search ..................... 514/486, 487, 514/590, 614, 520, 521, 522, 523, 476, 538, 595; 564/148, 36, 56, 142; 560/24, 29; 558/391

[56] References Cited

U.S. PATENT DOCUMENTS

| | | | |
|---|---|---|---|
| 3,177,251 | 4/1965 | Carron et al. | 564/150 |
| 3,193,578 | 7/1965 | Coirre | 564/150 |
| 3,419,659 | 12/1968 | Cauro et al. | 424/60 |

FOREIGN PATENT DOCUMENTS

| | | |
|---|---|---|
| 254461 | 1/1988 | European Pat. Off. |
| 348257 | 12/1989 | European Pat. Off. |
| 424243 | 4/1991 | European Pat. Off. |
| 511031 | 10/1992 | European Pat. Off. |
| 1163847 | 12/1959 | Germany . |
| 839610 | 6/1960 | United Kingdom . |
| 1225358 | 3/1971 | United Kingdom . |
| WO 91/08201 | 6/1991 | WIPO . |

OTHER PUBLICATIONS

Lawton, G. et al., "Regioselectivity in the Photochemical Ring Contraction of 4-Diazopyrazolidine-3,5-diones to give Aza-β-lactams", *Journal of the Chemical Society, Perkin Transactions 1*, No. 4, Apr. 1987, London, pp. 885–897.

Chemical Abstracts, vol. 84, No. 21, May 24, 1976, Columbus, Ohio, Abstract No. 150168j, "Acylation of ethanolhydrazones", p. 508.

Chemical Abstracts, vol. 76, No. 7, Feb. 14, 1972, Columbus, Ohio, Abstract No. 33754w, "Synthesis of hydrazino amines with potential antitubercular activity. VIII. Preparation of N-acetyl-N-(2-cyanoethyl)hydrazones of ketones", p. 280.

Chemical Abstracts, vol. 68, No. 11, Mar. 11, 1968, Columbus, Ohio, Abstract No. 49206q, "Acylation of some urea derivatives", p. 4750.

Chemical Abstracts, vol. 66, No. 19, May 8, 1967, Columbus, Ohio, Abstract No. 85980e, "Nucleic acid components and their analogs, LXXXVII. The preparation of 1-amino-5,6-dohydrouracil", p. 8063.

Chemical Abstracts, vol. 76, No. 1, Jan. 3, 1972, Columbus, Ohio, Abstract No. 3521a, "Preparation and cyanoetylation of some hydrazine derivatives", p. 312.

Hoffmann, U. and Jacobi, B., "Amino nitriles and their conversion products", Chemical Abstracts, vol. 28, p. 5473, 1934.

*Primary Examiner*—Shailendra Kumar
*Attorney, Agent, or Firm*—Bell Seltzer Intellectual Property Law Group of Alston & Bird LLP

[57] ABSTRACT

Novel monoamine oxidase B inhibitors of formula (I), wherein $R_1$=H, an optionally substituted benzyloxy or phenylethoxy group; p=0–3; $R_3$=H, a CN, OH, CCH group, a $C_1$–$C_3$ alkoxy-carbonyl group, or a $C_1$–$C_3$ alkylated cyanomethyl group; $R_2$=H or a $C_1$–$C_3$ alkyl group; n=0 or 1; if n=0, $R_4$ is a $C_1$–$C_3$ alkyl group or a $C_1$–$C_3$ alkoxy group, while if n=1, y=1 and $R_4$ is a $C_1$–$C_3$ alkyl group, a $C_1$–$C_3$ alkoxy group or a phenyl group. The invention also concerns processes for the preparation of said novel inhibitors and the therapeutic use thereof.

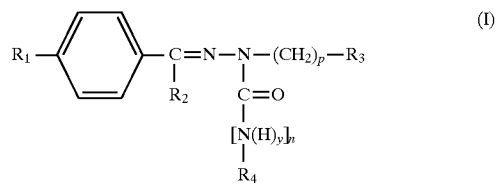

13 Claims, 4 Drawing Sheets

FIG.2A  MAO A

MAO B

MONOAMINE OXIDASE B INHIBITORS, PROCESSES FOR THEIR PREPARATION AND USE THEREOF

This application is a 371 of PCT/Fr95/0006, filed Jan. 19, 1995.

The subject of the present invention is monoamine oxidase B inhibitors, processes for their preparation and their use in therapy.

Monoamine oxidases (MAO) are enzymes, located mainly in the outer membrane of the mitochondria and responsible for metabolizing a number of monoamines acting as neurotransmitters in mammals.

In the human body, the principal monoamines which are deaminated by MAOs belong either to the indole series: tryptamine and 5-hydroxytryptamine or serotonin, or to the aromatic amino acid series: tyramine and catecholamines such as dopamine, noradrenaline and adrenaline.

Two principal forms of MAO can be currently identified in the body: an A form which is thought to convert more particularly serotonin and noradrenaline, and a B form whose preferred substrates are benzylamine and phenylethylamine, both forms converting, in a roughly equivalent manner, dopamine, tyramine and tryptamine.

Some organs appear to express only one of the two enzymes whereas both forms are simultaneously present in other tissues such as the liver or the brain.

Given that the hypotheses relating to the bio-chemical mechanisms of depression involve certain mono-amines such as serotonin and catecholamines, it was proposed, from 1957, to use MAO inhibitors in the treatment of this pathology.

So far, three generations of MAO inhibitors have appeared in succession:

1/ So-called "mixed" and "irreversible" inhibitors:

The major one among them is phenelzine (NARDELZINE®) and iproniazide (MARSILID®).

The structure common to these inhibitors is a hydrazine group.

They are termed "mixed" because they inhibit both forms of MAO. They are termed "irreversible" because they form a covalent bond with these enzymes which results in an irreversible inactivation of said enzymes which comes to an end only well after stopping the treatment, when the newly synthesized enzymes have taken over (15 to 21 days). In addition, they are responsible for a modification of blood pressure resulting in undesirable blood pressure disorders: hypotension, vertigo, dizziness, hypothymic and even syncopal tendencies.

2/ "Selective" and "irreversible" inhibitors:

This second generation of MAOIs includes three families of compounds which are the arylhydrazines, the propargylics and the cyclopropylamines.

These compounds preferably act on either form of the MAOS. Thus, for example, among the propargylic inhibitors, clorgyline and pargyline inhibit MAO A whereas deprenyl acts on MAO B.

It should however be noted that, although inhibiting the MAOs, some of these compounds, such as pargyline and deprenyl, lack antidepressant effects and have been indicated in the treatment of Parkinson's disease, in combination with L-dopa.

In addition, all these compounds act by first binding noncovalently to the MAOs, and then by forming with them irreversible covalent complexes, limiting their manageability because of the persistence of their action well after stopping the treatment.

Thus, for example, a general anesthetic can only be envisaged in a patient treated with this type of MAOI after a period of about three weeks after stopping the treatment.

3/ "Selective" and "reversible" inhbitors:

These third-generation inhibitors include:

derivatives of harmala, alkaloids from *Peganum harmala*, which are selective and reversible inhibitors of MAO A, with a very short duration of action;

phenylalkylamines, which are selective inhibitors of MAO A;

derivatives of oxazolidinones, which are selective inhibitors of MAO A and which have as principal representative toloxatone (HUMORYL®) These compounds are described in EP 0,424,243, EP 0,428,421 and EP 0,511,031.

Although the use of these compounds represents a definite advance in therapy because of their rapidly reversible activity (in less than 24 hours), some physiopathological studies relating to senile dementia and Alzheimer's disease appear to show a most special advantage in using the B MAOIs.

Indeed, in these pathologies, a high increase in the MAO B/MAO A ratio is observed which is accompanied by an increase in a destructive activity of the MAOs. The decrease in the number of neurons producing dopamine linked with cellular aging also contributes to this physiological phenomenon. A possible inhibition of MAO B by selective and reversible products should make it possible to reequilibrate the ratio between the two forms of enzyme in favor of MAO A, and thus to improve the condition of the subjects.

Patent Applications EP 0,348,257 and WO 91/08201 propose derivatives of 4-(arylmethyloxy)phenyldiazole, essentially represented by tetrazoles, which appear to exhibit an anti-MAO activity which is selective against MAO B. However, no information is available, as regards the compounds described in this application, on the reversibility of their activity, or a decline both from the pharmacological and toxicological point of view.

The applicants consequently set themselves the objective of providing novel inhibitors of MAO B exhibiting both selectivity and reversibility toward MAO B, conferring on them great therapeutic manageability.

The subject of the present invention is therefore the use of a compound corresponding to the following formula (I):

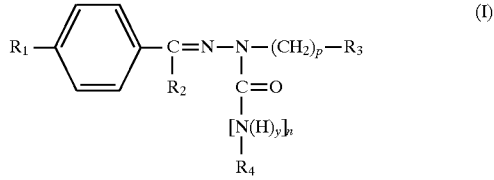

in which:

$R_1$ represents a hydrogen atom, a benzyloxy group or a phenylethoxy group whose phenyl ring is optionally substituted;

p is an integer from 0 to 3;

$R_3$ represents a hydrogen atom, a CN group, a hydroxyl group, a CCH group, a ($C_1$–$C_3$ alkoxy)carbonyl group or a $C_1$–$C_3$ alkylated cyanomethyl group;

$R_2$ represents a hydrogen atom or a $C_1$–$C_3$ alkyl group;

n is equal to 0 or 1, in which case:

if n=0, $R_4$ represents a $C_1$–$C_3$ alkyl group or a $C_1$–$C_3$ alkoxy group; whereas if n=1, y=1 and $R_4$ represents a $C_1$–$C_3$ alkyl group, a $C_1$–$C_3$ alkoxy group or a phenyl group;

for the preparation of a medicinal product having a monoamine oxidase B inhibiting activity.

The compounds of formula (I) as defined above include their various isomers.

In the preceding text and in the text which follows, the expression "$C_1$–$C_3$ alkyl" designates hydrocarbon groups comprising 1 to 3 carbon atoms, namely methyl, ethyl, n-propyl and i-propyl; the expression "$C_1$–$C_3$ alkoxy" corresponds to the formula O-($C_1$–$C_3$ alkyl); the expression "($C_1$–$C_3$ alkoxy)carbonyl" represents a formula COO-($C_1$–$C_3$ alkyl); the term halogen designates chlorine, fluorine, bromine or iodine.

The compounds of formula (I), as defined above, are particularly useful for the preparation of a medicinal product having a monoamine oxidase B inhibiting activity because they are capable of inhibiting MAO B both selectively and reversibly while lacking toxic effects.

For this, they may be used alone or in combination, optionally with one or more other active ingredients and/or adjuvants which are pharmaceutically compatible.

Preferably, $R_1$ represents a benzyloxy group whose phenyl ring is optionally substituted with one or more halogen atoms and/or one or more $NO_2$ groups and/or one or more $C_1$–$C_3$ alkyl groups and/or one or more $C_1$–$C_3$ alkoxy groups.

Among the compounds of formula (I), some have already been described as being capable of having therapeutic applications. However, these relate to the treatment of tuberculosis (STRUMILLO and GRUDZINSKI, Acta Pol. Pharm., 1971, 28, 247–251) and the treatment of rhinopharyngeal viral conditions (U.S. Pat. No. 3,867,425) in which monoamine oxidase B inhibition is not at all sought.

The subject of the invention is therefore also novel medicinal products which comprise at least one active ingredient corresponding to one of the following specific formulae:

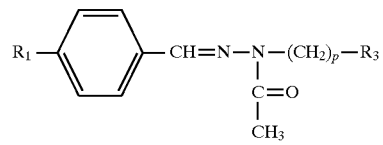

(I-a)

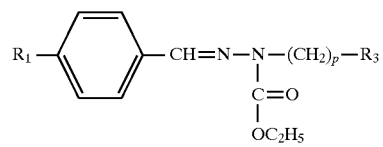

(I-b)

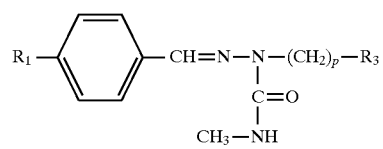

(I-c)

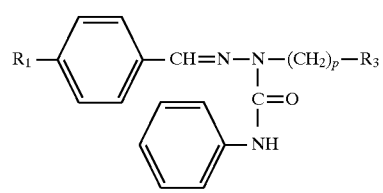

(I-d)

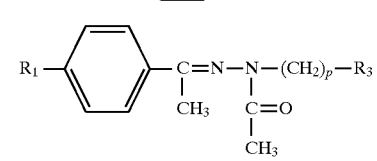

(I-e)

in which:
$R_1$ represents a hydrogen atom, a benzyloxy group or a phenylethoxy group whose phenyl ring is optionally substituted, provided that $R_1$ is different from a hydrogen atom in the specific formula (I-e);

p is an integer from 0 to 3; and $R_3$ represents a CN group, an OH group, a CCH group, a ($C_1$–$C_3$ alkoxy)carbonyl group or a $C_1$–$C_3$ alkylated cyano-methyl group.

These medicinal products find application especially in the treatment of conditions in which [lacuna] inhibition of monoamine oxidase B such as for example depressive syndromes.

Among the medicinal products in accordance with the invention, there are preferred especially those comprising, as active ingredient(s), the compounds of specific formulae (I-a), (I-b), (I-c), (I-d) and (I-e), presented in Table 1 below:

TABLE 1

| Code No. | $R_1$ | p | $R_3$ |
|---|---|---|---|
| I-a1 | H | 2 | CN |
| I-a2 | benzyloxy | 2 | CN |
| I-a2.1 | (4-methylbenzyl)oxy | 2 | CN |
| I-a2.2 | (4-nitrobenzyl)oxy | 2 | CN |
| I-a2.3 | (4-chlorobenzyl)oxy | 2 | CN |
| I-a2.4 | (4-methoxybenzyl)oxy | 2 | CN |
| I-a2.5 | (2,4-dichlorobenzyl)oxy | 2 | CN |
| I-a2.6 | (2-chlorobenzyl)oxy | 2 | CN |
| I-a3 | H | 2 | OH |
| I-a4 | benzyloxy | 2 | OH |
| I-a5 | benzyloxy | 2 | $COOCH_3$ |
| I-a6 | phenylethoxy | 2 | CN |
| I-a7 | benzyloxy | 1 | CH—CN<br>\|<br>$CH_3$ |
| I-a8 | benzyloxy | 1 | CN |
| I-a9 | benzyloxy | 3 | CN |
| I-a10 | benzyloxy | 1 | CCH |
| I-b1 | H | 2 | CN |
| I-b2 | benzyloxy | 2 | CN |
| I-b3 | H | 2 | OH |
| I-b4 | benzyloxy | 2 | OH |
| I-c1 | H | 2 | CN |
| I-c2 | benzyloxy | 2 | CN |
| I-c3 | H | 2 | OH |
| I-c4 | benzyloxy | 2 | OH |
| I-d1 | H | 2 | CN |
| I-d2 | benzyloxy | 2 | CN |
| I-e1 | benzyloxy | 2 | CN |

In a preferred embodiment of a medicinal product in accordance with the invention, the latter comprises, as active ingredient, 4-(benzyloxy)benzaldehydeacetyl-(2-cyanoethyl)hydrazone (compound I-a2).

Among the compounds corresponding to the specific formulae (I-a), (I-b), (I-c), (I-d) and (I-e), some have already been described, either as sunscreens (U.S. Pat. No. 3,419,659), or as products resulting from the acylation of urea (NOVACEK, Collect. Czech. Chem. Commun., 1967 32, 1712–1718) or alternatively as pesticides (GADZHIEV and BUDAGOV, Azerb. Khim. Zh., 1975, 5, 47–48).

The subject of the invention is therefore also new compounds which correspond to the following specific formulae:

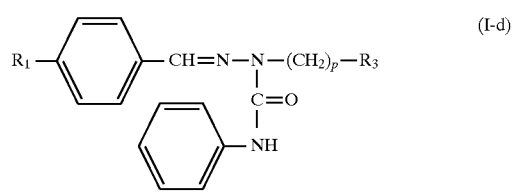

(I-d)

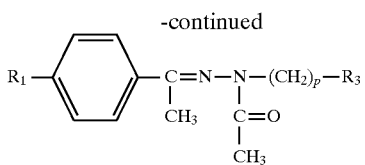

in which:
- $R_1$ represents a hydrogen atom, a benzyloxy group or a phenylethoxy group whose phenyl ring is optionally substituted, provided that $R_1$ is different from a hydrogen atom in the specific formula (I-e);
- p is an integer from 0 to 3; and
- $R_3$ represents a CN group, an OH group, a CCE group, a ($C_1$–$C_3$ alkoxy)carbonyl group or a $C_1$–$C_3$ alkylated cyanomethyl group.

The subject of the present invention is, moreover, a process for the preparation of a compound of specific formula (I-d) as defined above, which comprises:

1) a condensation reaction between an aromatic aldehyde of formula:

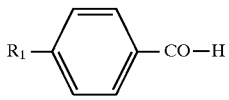

in which:
- $R_1$ represents a hydrogen atom, a benzyloxy or phenylethoxy group whose phenyl ring is optionally substituted; and a hydrazine of formula: $NH_2$—$NH$—$(CH_2)_p$–$R_3$ in which:
- p is an integer from 0 to 3;
- $R_3$ represents a CN group, an OH group, a CCH group, a ($C_1$–$C_3$ alkoxy)carbonyl group or a $C_1$–$C_3$ alkylated cyanomethyl group;

2) a reaction of acylation of the product derived from reaction 1) by means of a reagent such as phenyl isocyanate.

Moreover, all the compounds of formula (I) can be obtained by this process.

Thus, for example, for the preparation of the compounds of specific formulae (I-a) and (I-b), the acylation of the product derived from reaction 1) (condensation reaction between the aromatic aldehyde and hydrazine) is performed by means of a reagent of formula: $R_4$—CO—Cl in which $R_4$ represents a methyl group or an ethoxy group whereas for the preparation of the compounds corresponding to the specific formula (I-c), the same acylation reaction is performed by means of methyl isocyanate.

The subject of the invention is also a process for the preparation of a compound of specific formula (I-e), which process comprises:

1) a condensation reaction between an aromatic aldehyde of formula:

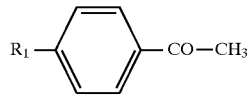

in which:
- $R_1$ represents a benzyloxy or phenylethoxy group whose phenyl ring is optionally substituted; and:
  * either a hydrazine of formula: $NH_2$—$NH$—$(CH_2)_p$— $R_3$ in which:
  p is a integer from 0 to 3;
  $R_3$ represents a CN group, an OH group, a CCH group, a ($C_1$–$C_3$ alkoxy)carbonyl group or a $C_1$–$C_3$ alkylated cyanomethyl group;
  * or the hydrazine of formula: $NH_2$—$NH$—$CO$—$CH_3$ 2) a reaction:
  * either for acylation of the product derived from reaction 1) by a reagent such as acetyl chloride;
  * or for alkylation of the product derived from reaction 1) by a reagent of formula: Hal—$(CH_2)_p$—C≡Z in which:
- p is an integer from 0 to 3;
- Hal represents a halogen atom;
- Z represents a CH group or a nitrogen atom, or by a reagent of formula: Br—$(CH_2)_p$—COO—($C_1$–$C_3$ alkyl)

in which p is an integer from 0 to 3.

Advantageously, the alkylation reaction is performed with a reagent chosen from bromoacetonitrile, 4-bromobutyronitrile, propargyl bromide or methyl 3-bromopropionate in the presence of one or more solvents chosen from anhydrous pyridine, anhydrous ethyl acetate, anhydrous benzene or acetic acid.

The subject of the invention is finally a process for the treatment of conditions in which inhibition of monoamine oxidase B is desired, which process consists in administering to a human or animal host an effective quantity of at least one compound of formula (I) as defined above.

In addition to the preceding features, the invention also comprises other features which will emerge from the description which will follow, made by way of examples and with reference to the accompanying drawing in which.

Figure 1:
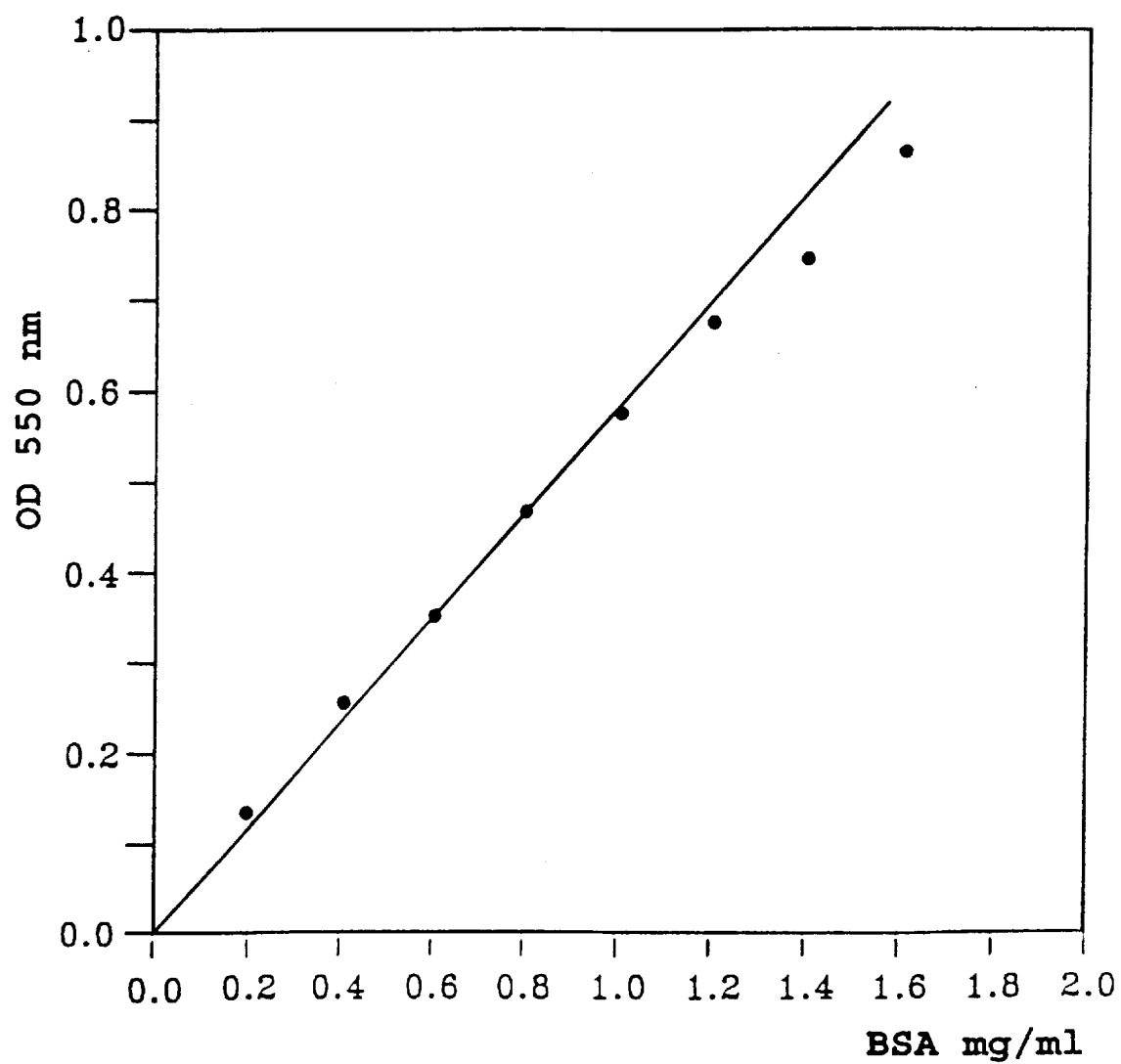
FIG. 1 represents a calibration series to determine the protein concentration of a mitochondrial suspension.

It should be clearly understood, however, that these examples are given solely by way of illustrations of the subject of the invention and do not constitute in any manner a limitation thereto.

EXAMPLES

Example 1: Preparation of the compound (I-a1):
Benzaldehyde acetyl(2-cyanoethyl)hydrazone
1.1 Preparation of benzaldehyde (2-cyanoethyl)hydrazone:

Benzaldehyde (2-cyanoethyl)hydrazone is prepared by condensation of benzaldehyde with (2-cyanoethyl) hydrazine according to the following procedure:

$10^{-2}$ moles of (2-cyanoethyl)hydrazine are added to a solution containing $10^{-2}$ moles of benzaldehyde in 20 ml of ethanol. The reaction is left under reflux for 30 minutes. At the end of the reaction, the mixture is cooled. After evaporation of the solvents, the product obtained is in the form of an extremely unstable oil. The crude reaction yield is 81%.

(2-Cyanoethyl)hydrazine can be obtained by a MICHAEL reaction (HOFFMAN V. and JACOBI B., Chemical Abstracts, Vol. 28, p 5473, 1934), that is to say by the action of hydrazine in excess on one mole of acrylonitrile in ethanol.

1.2 Acylation of benzaldehyde (2-cyanoethyl)hydrazone with acetyl chloride:

0.78 g ($10^{-2}$ moles) of acetyl chloride is added dropwise to a solution containing $10^{-2}$ moles of benzaldehyde (2-cyanoethyl)hydrazone and 0.79 g ($10^{-2}$ moles) of anhydrous pyridine in 20 ml of anhydrous ethyl acetate, with stirring in the cold.

The mixture is slowly heated to reflux temperature and left stirring for 2 hours, and then filtered hot. After cooling the filtrate, the product crystallizes. It is filtered. An additional quantity of the latter is obtained by evaporation of the filtrate. The product obtained at the end of the reaction is washed with 10 ml of water and then dried and recrystallized from ethanol. The product has a melting point equal to 109° C. The reaction yield is 54%.

Example 2: Preparation of the compound (I-a2): 4-(Benzyloxy)benzaldehyde acetyl(2-cyanoethyl) hydrazone 2.1 Preparation of 4- (benzyloxy)benzaldehyde (2-cyanoethyl)hydrazone:

4-(benzyloxy)benzaldehyde (2-cyanoethyl)hydrazone is prepared by condensation of 4-(benzyloxy)benzaldehyde with (2-cyanoethyl)hydrazine according to the following procedure:

$10^{-2}$ moles of (2-cyanoethyl)hydrazine are added to a solution containing $10^{-2}$ moles of 4-(benzyloxy) benzaldehyde in 20 ml of ethanol. The reaction is left under reflux for 30 minutes. At the end of the reaction, the product precipitates. After filtration, it is recovered and recrystallized twice from ethanol. The reaction yield is 86%.

2.2 Acylation of 4-(benzylozy)benzaldehyde (2-cyanoethyl)hydrazone with acetyl chloride:

This acylation reaction is carried out according to a procedure identical to that described in 1.2 of Example 1 above, starting with, on the one hand, a solution containing $10^{-2}$ moles of 4-(benzyloxy)benzaldehyde (2-cyanoethyl) hydrazone and 0.79 g ($10^{-2}$ moles) of anhydrous pyridine in 20 ml of anhydrous ethyl acetate and, on the other hand, 0.78 g ($10^{-2}$ moles) of acetyl chloride. It makes it possible to obtain the compound (I a2) with a yield of 50%. It has a melting point of 150° C.

Example 3: Preparation of the compound (I-a3): Benzaldehyde acetyl(2-hydroxyethyl)hydrazone 3.1 Preparation of benzaldehyde (2-hydroxyethyl) hydrazone:

Benzaldehyde (2-hydroxyethyl)hydrazone is prepared by condensation of benzaldehyde with (2-hydroxyethyl) hydrazine according to the following procedure: $10^{-2}$ moles of (2-hydroxyethyl)hydrazine are added to a solution containing $10^{-2}$ moles of benzaldehyde in 20 ml of ethanol. The reaction is left under reflux for 30 minutes. The mixture is then cooled. The solvents are removed by evaporation. The product obtained is an extremely unstable oil. The crude reaction yield is 97%.

(2-hydroxyethyl)hydrazine is a product marketed by ALDRICH.

3.2 Acylation of benzaldehyde (2-hydroxyethyl)hydrazone with acetyl chloride:

0.78 g ($10^{-2}$ moles) of acetyl chloride is added dropwise to a solution containing $10^{-2}$ moles of benzaldehyde (2-hydroxyethyl)hydrazone and 0.79 g ($10^{-2}$ moles) of anhydrous pyridine in 20 ml of anhydrous ethyl acetate, with stirring in the cold.

The reaction mixture is left at 0° C., with stirring, for 2 hours until it is filtered. The product obtained at the end of the reaction is washed with 10 ml of water and then dried and recrystallized from ethanol. The reaction yield is 34%. The product has a melting point of 110° C.

Example 4: Preparation of the compound (I-a4): 4-(Benzyloxy)benzaldehyde acetyl(2-hydroxyethyl) hydrazone 4.1 Preparation of (4-benzylozy)benzaldehyde (2-hydroxyethyl)hydrazone:

4-(benzyloxy)benzaldehyde (2-hydroxyethyl)hydrazone is obtained by condensation of 4-(benzyloxy)benzaldehyde with (2-hydroxyethyl)hydrazine by reacting, for example, a solution containing $10^{-2}$ moles of (4-benzyloxy) benzaldehyde in 20 ml of ethanol with $10^{-2}$ moles of (2-hydroxyethyl)hydrazine. The reaction is left at reflux for 30 minutes, at the end of which the mixture is cooled and the hydrazone obtained precipitates. After filtration, it is recovered and recrystallized twice from ethanol. It has a melting point of 91° C. The reaction yield is 79%.

4.2 Acylation of 4-(benzyloxy)benzaldehyde (2-hydroxyethyl)hydrazone with acetyl chloride:

It is carried out according to a procedure identical to that described in point 3.2 of Example 3 above, starting, on the one hand, with a solution containing $10^{-2}$ moles of 4-(benzyloxy)benzaldehyde (2-hydroxyethyl)hydrazone and 0.79 g ($10^{-2}$ moles) of anhydrous pyridine in 200 ml of anhydrous ethyl acetate and, on the other hand, 0.78 g ($10^{-2}$ moles) of acetyl chloride.

It makes it possible to obtain the compound (I a4) with a yield of 38%. It has a melting point of 131° C.

Example 5: Preparation of the compound (I-a2.6): 4-[(2-Chlorobenzyl)oxy]benzaldehyde acetyl(2-cyanoethyl)hydrazone The compound (I-a2.6) is obtained by an alkylation reaction in situ performed according to the following procedure:

0.43 g ($5.1 \times 10^{-3}$ moles) of 2-(cyanoethyl)hydrazine is added, at room temperature, with stirring, to a solution of $5 \times 10^{-3}$ moles of 4-[(2-chlorobenzyl)oxy]benzaldehyde in 20 ml of anhydrous benzene. The reaction mixture is heated to reflux temperature and the water formed during the reaction is removed by azeotropic distillation. The solution is then adjusted to 10° C. and 0.40 g ($5.1 \times 10^{-3}$ moles) of anhydrous pyridine and 0.39 g ($5.1 \times] 10^{-3}$ moles) of acetyl chloride are added successively. The mixture is left stirring at room temperature for 30 minutes. The benzene is then removed by evaporation under vacuum. The residue obtained is dissolved in 100 ml of dichloromethane and the resulting organic phase is washed three times with water. It is then dried over magnesium sulfate and then evaporated. The residue is crystallized from ethanol. It has a melting point of 142° C. The reaction yield is 51%.

Example 6: Preparation of the compound (I-a2.5): 4-[(2,4-Dichlorobenzyl)oxy]benzaldehyde acetyl(2-cyanoethyl)hydrazone The compound (I-a2.5) is prepared according to a procedure identical to that described in Example 5, from 4-[(2, 4-dichlorobenzyl)oxy]benzaldehyde and 2-(cyanoethyl) hydrazine.

The compound (I-a2.5) has a melting point of 137° C. The reaction yield is 38%.

Example 7: Preparation of the compound (I-a6): 4-(2-Phenylethozy)benzaldehyde acetyl(2-cyanoethyl) hydrazone The compound (I-a6) is prepared according to a procedure identical to that described in Example 5, from 4-(2- phenylethoxy)benzaldehyde and 2-(cyanoethyl)hydrazine. It has a melting point of 129° C. The reaction yield is 55%.

Example 8: Preparation of the compound (I-a7): 4-(Benzyloxy)benzaldehydeacetyl(2-cyanopropyl) hydrazone 0.64 g ($5.1 \times 10^{-3}$ moles) of 2-(cyanopropyl)hydrazine is added, at room temperature and with stirring, to a solution of $5 \times 10^{-3}$ moles of 4-(benzyloxy)benzaldehyde in 20 ml of anhydrous benzene. The reaction mixture is heated to reflux temperature and the water formed during the reaction is removed by azeotropic distillation. The solution is then adjusted to 10° C. and 0.40 g ($5.1 \times 10^{-3}$ moles) of anhydrous pyridine and 0.39 g ($5.1 \times 10^{-3}$ moles) of acetyl chloride are added successively. The mixture is left stirring at room temperature for 30 minutes. The benzene is then removed by evaporation under vacuum. The residue obtained is dissolved in 100 ml of dichloromethane and the resulting organic phase is washed three times with water. It is then dried over magnesium sulfate and then evaporated. The residue is recrystallized from ethanol. It has a melting point of 106° C. The reaction yield is 42%.

Example 9: Preparation of the compound (I-a5): 4-(Benzyloxy)benzaldehyde acetyl (2-methoxycarbonylethyl) hydrazone 9.1 Preparation of 4-(benzyloxy)benzaldehyde acetylhydrazone:

A solution of $10^{-2}$ moles of acetylhydrazine (0.74 g) in 20 ml of ethanol is added to $10^{-2}$ moles of 4-(benzyloxy) benzaldehyde (2.12 g) in 20 ml of ethanol. The reaction mixture is heated to reflux temperature for 90 minutes, at the end of which the solution is slowly adjusted to 0° C. The product obtained precipitates. It is filtered, drained and recrystallized from ethanol. Melting point: 170° C. Reaction yield: 76%.

9.2 Alkylation of 4-(benzyloxy)benzaldehyde acetylhydrazone:

A solution of $5 \times 10^{-3}$ moles of 4-(benzyloxy) benzaldehyde acetylhydrazone (1.34 g) in 5 ml of anhydrous DMF is added to $5 \times 10^{-3}$ moles of sodium hydride (0.12 g) in suspension in 10 ml of anhydrous DMF. The reaction mixture is heated slowly on a water bath at 80° C. for 30 minutes. After cooling, a solution containing 0.85 g ($5.1 \times 10^{-3}$ moles) of methyl 3-bromopropionate in 5 ml of DMF is slowly added to the mixture. The latter is stirred for one hour at room temperature, then it is poured into 100 ml of ice-cold water. A product precipitates. After standing for 30 minutes, it is filtered, subjected to draining, at the end of which it is chromatographed on a MACHEREY-NAGEL silica gel 60 (0.04–0.063 ml) using a mixture of ethyl acetate and dichloromethane (1/9) as eluent. The oil obtained precipitates. The compound (I-a5) is slowly recrystallized from ether. Its melting point is 170° C. The reaction yield is 11%.

Example 10: Preparation of the compound (I-a8): 4-(Benzylozy)benzaldehyde acetyl(cyanomethyl)hydrazone The compound (1-a8) is obtained by an alkylation reaction of 4-(benzyloxy)benzaldehyde acetylhydrazone, prepared in accordance with point 9.1 of Example 9 above, with bromoacetonitrile.

The alkylation with bromoacetonitrile is performed according to the following procedure: a solution of $5 \times 10^{-3}$ moles of 4-(benzyloxy)benzaldehyde acetylhydrazone (1.34 g) in 5 ml of anhydrous DMF is added to $5 \times 10^{-3}$ moles of sodium hydride (0.12 g) in suspension in 10 ml of anhydrous DMF. The reaction mixture is heated slowly on a water bath at 80° C. for 30 minutes. After cooling, a solution containing 0.61 g ($5.1 \times 10^{-3}$ moles) of 3-bromoacetonitrile in 5 ml of DMF is slowly added to the mixture. The latter is stirred for one hour at room temperature and then it is poured into 100 ml of ice-cold water. A product precipitates. After standing for 30 minutes, it is filtered, drained and then recrystallized from ethanol. The compound (I-a8) has a melting point of 136° C. The reaction yield is 59%.

Example 11: Preparation of the compound (I-a9): 4-(Benzyloxy)benzaldehyde acetyl(3-cyanopropyl) hydrazone The compound (1-a9) is obtained by an alkylation reaction of 4-(benzyloxy)benzaldehyde acetylhydrazone, prepared as described in point 9.1 of Example 9 above, with 4-bromobutyronitrile.

The alkylation reaction is performed according to a procedure identical to that described in Example 10 above, with the aid of a solution containing 0.75 g ($5.1 \times 10^{-3}$ moles) of 4-bromobutyronitrile in 5 ml of DMF. It has a yield of 75%. The compound (I-a9) obtained has a melting point of 103° C.

Example 12: Preparation of the compound (I-a10): 4-(Benzyloxy)benzaldehyde acetylpropargylhydrazone This compound is obtained by an alkylation reaction of 4-(benzyloxy)benzaldehyde acetylhydrazone, prepared as described in point 9.1 of Example 9, with propargyl bromide.

The alkylation reaction is performed according to a procedure identical to that described in Example 10 above, with the aid of a solution containing 0.60 g ($5.1 \times 10^{-3}$ moles) of propargyl bromide in 5 ml of DMF, with a yield of 54%. The compound (I-a10) has a melting point of 120° C.

Example 13: Preparation of the compound (I-b1): Benzaldehyde (2-cyanoethyl)(ethoxycarbonyl) hydrazone 13.1 Preparation of benzaldehyde (2-cyanoethyl)hydrazone:

Benzaldehyde (2-cyanoethyl)hydrazone is prepared using a procedure identical to that described in point 1.1 of Example 1.

13.2 Acylation of benzaldehyde (2-cyanoethyl)hydrazone with ethyl chloroformate:

1.08 g ($10^{-2}$ moles) of ethyl chloroformate in solution in 5 ml of anhydrous ethyl acetate are added dropwise to a solution containing $10^{-2}$ moles of benzaldehyde (2-cyanoethyl)hydrazone and 0.79 g ($10^{-2}$ moles) of anhydrous pyridine in 20 ml of anhydrous ethyl acetate, with stirring in the cold. The reaction mixture is slowly heated to reflux temperature and left stirring for 2 hours and then filtered hot.

After cooling of the filtrate, the product crystallizes. It is filtered. An additional quantity of product may be obtained by evaporation of the filtrate. The product is washed with 10 ml of water and then dried and recrystallized from a mixture of ethyl acetate and petroleum ether. It has a melting point of 91° C. The reaction yield is 48%.

Example 14 Preparation of the compound (I-b2): 4-(Benzylozy)benzaldehyde (2-cyanoethyl) (ethoxycarbonyl)hydrazone 14.1 Preparation of 4-(benzyloxy)benzaldehyde (2-cyanoethyl)hydrazone:

4-(Benzyloxy)benzaldehyde (2-cyanoethyl)hydrazone is obtained according to a procedure identical to that described in point 2.1 of Example 2 above.

14.2 Acylation of 4-(benzyloxy)benzaldehyde (2-cyanoethyl)hydrazone with ethyl chloroformate:

It is carried out according to a procedure identical to that described in point 13.2 of Example 13 above, starting with, on the one hand, a solution containing $10^{-2}$ moles of 4-(benzyloxy)benzaldehyde (2-cyanoethyl)hydrazone and 0.79 g ($10^{-2}$ moles) of anhydrous pyridine in 20 ml of anhydrous ethyl acetate and, on the other hand, a solution containing 1.08 g ($10^{-2}$ moles) of ethyl chloroformate in 5 ml of anhydrous ethyl acetate.

The product obtained is recrystallized from ethanol. The reaction yield is 71%. The product has a melting point equal to 100° C.

Example 15: Preparation of the compound (I-b3): Benzaldehyde (2-hydroxyethyl)(ethoxycarbonyl) hydrazone This compound is obtained by an acylation reaction of benzaldehyde (2-hydroxyethyl)hydrazone, prepared according to point 3.1 of Example 3, with ethyl chloroformate.

This acylation is performed in the following manner: 1.08 g ($10^{-2}$ moles) of ethyl chloroformate in 5 ml of anhydrous ethyl acetate are added dropwise to a solution containing $10^{-2}$ moles of benzaldehyde (2-hydroxyethyl)hydrazone and 0.79 g ($10^{-2}$ moles) of anhydrous pyridine in 20 ml of anhydrous ethyl acetate, with stirring in the cold. The reaction mixture is left at 0° C. with stirring for 2 hours and then it is filtered. The product obtained is washed with 10 ml of water and then dried and recrystallized from a mixture of ethyl acetate and petroleum ether. It has a melting point of 69.5° C. The reaction yield is 62%.

Example 16: Preparation of the compound (I-b4): 4-(Benzyloxy)benzaldehyde (2-hydroxyethyl) (ethoxycarbonyl)hydrazone This compound is obtained by an acylation reaction of 4-(benzyloxy)benzaldehyde (2-hydroxyethyl)hydrazone, prepared according to point 4.1 of Example 4 above, with ethyl chloroformate.

The acylation reaction is carried out according to a procedure identical to that described in Example 15 above, with the exception of the recrystallization of the product which is obtained from ethanol. The yield of this acylation reaction is 71%. The product has a melting point equal to 118° C.

Example 17: Preparation of the compound (I-c1): Benzaldehyde (2-cyanoethyl)(N-methylcarbamoyl) hydrazone 17.1 Preparation of benzaldehyde (2-cyanoethyl)hydrazone:

Benzaldehyde (2-cyanoethyl)hydrazone is obtained according to the procedure described in point 1.1 of Example 1 above.

17.2 Acylation of benzaldehyde (2-cyanoethyl)hydrazone with methyl isocyanate:

0.57 g ($10^{-2}$ moles) of methyl isocyanate is added, at 25° C., to a solution of $10^{-2}$ moles of benzaldehyde (2-cyanoethyl)hydrazone in 30 ml of anhydrous benzene. The mixture is then heated to boiling temperature and left under reflux for 30 minutes. On cooling, the acylated compound crystallizes. It is filtered, drained and then recrystallized from a mixture of benzene and cyclohexane. Its melting point is 145° C. The reaction yield is 48%.

Example 18: Preparation of the compounds (I-c2), (I-c3) and (I-c4):

The compounds (I-c2), (1-c3) and (I-c4) are obtained by an acylation reaction of respectively 4-(benzyloxy) benzaldehyde (2-cyanoothyl)hydrazone, benzaldehyde (2-hydroxyethyl) hydrazone and 4-(benzyloxy)benzaldehyde (2-hydroxyethyl)hydrazone, with methyl isocyanate.

The (2-cyanoethyl)hydrazones and the (2-hydroxyethyl) hydrazones of aromatic aldehydes are prepared according to points 2.1 of Example 2, 3.1 of Example 3 and 4.1 of Example 4.

The acylation reaction of these hydrazones of aromatic aldehydes with methyl isocyanate is carried out according to a procedure identical to that described in point 17.2 of Example 17 above, except for the recrystallization of the compound (I-c4) which is obtained from ethanol.

The yield of this acylation is respectively:

- 41% for the compound (I-c2) [4-(benzyloxy) benzaldehyde (2-cyanoethyl)(N-methylcarbamoyl) hydrazone], whose melting point is 152° C.,
- 35% for the compound (I-c3) [benzaldehyde (2-hydroxyethyl)(N-methylcarbamoyl)hydrazone], whose melting point is 141.5° C.,
- 42% for the compound (I-c4)[4-(benzyloxy) benzaldehyde (2 -hydroxyethyl) (N-methylcarbamoyl) hydrazonel, whose melting point is 196° C.

Example 19: Preparation of the compounds (I-d1) and (I-d2):

The compounds (I-d1) and (I-d2) are prepared by an acylation reaction in situ performed according to the following procedure: 0.8 g ($10^{-2}$ moles) of (2-cyanoethyl) hydrazine is added to a solution of 1 g ($10^{-2}$ moles) of benzaldehyde (for the preparation of the compound (I-d1)) or of 4-(benzyloxy)benzaldehyde (for the preparation of the compound (I-d2)) in 30 ml of anhydrous benzene. The reaction mixture is heated to boiling temperature until disappearance of the aldehyde, whose presence is detected by thin-layer chromatography. The water is then removed by azootropic distillation. The solution is then cooled to 25° C. 1.3 g (1.1×10$^{-2}$ moles) of phenyl isocyanate are then added. The mixture is heated at boiling temperature for 5 minutes. A white product forms. It is filtered and then washed with 5 ml of benzene. The recrystallization of the product is performed in butanol.

The reaction yield is:

- quantitative for the compound (I-d1) [benzaldehyde (2-cyanoothyl)(N-phanylcarbamoyl)hydrazone], whose melting point is 125° C.,
- equal to 51% for the compound (I-d2) [4-(benzyloxy) benzaldehyde (2-cyanoethyl) (N-phenylcarbamoyl) hydrazone], whose melting point is 194° C.

Example 20: Preparation of the compound (I-e1): 4-(Benzylozy)acetophenone acetyl(2-cyanoethyl) hydrazone 4.4×10$^{-3}$ moles (0.37 g) of 2-(cyanoothyl)hydrazine are added, at room temperature and with stirring, to a solution containing 0.99 g (4.4×10$^{-3}$ moles) of 4-(benzyloxy) acetophenone in 20 ml of anhydrous benzene, in the presence of a few drops of acetic acid. The reaction mixture is heated to reflux temperature and the water formed during the reaction is removed by azeotropic distillation. The solution is then adjusted to 10° C. and 4.4×10$^{-3}$ moles of anhydrous pyridine (0.34 g) and 4.4×10$^{-3}$ moles of acetyl chloride (0.34 g) are added successively. The mixture is left stirring at room temperature for 30 minutes. The benzene is then removed by evaporation under vacuum. The residue obtained is dissolved in 100 ml of dichloromethane and the resulting organic phase is washed three times with water. It is then dried over magnesium sulfate and then evaporated. The residue is recrystallized from ethanol. It has a melting point of 77° C. The reaction yield is 15%.

Example 21: Pharmacological studies:
21.1 Activity and selectivity

The compounds of formula (I) were tested in vitro in order to determine their inhibitory activity toward rat brain MAO A and MAO B and their selectivity toward these enzymes.
A/ Experimental procedure:
a) Preparation of the mitochondrial suspension:
  * Collection of the cerebral tissues Whistar rats weighing between 150 and 200 grams are killed by decapitation. The brain, with the exception of the cerebellum, is collected, weighed and homogenized using an Ultraturax (maximum speed for 5 seconds, five times in succession) in a 0.32M sucrose and 10 mM Tris buffer, pH 7.4 at 0° C., at the rate of 10 ml of buffer per gram of fresh tissue.
  * Preparation of the mitochondrial suspension The homogenate obtained above is centrifuged for 5 minutes at 1000 g in a refrigerated centrifuge (+4° C.). The supernatant is recovered and subjected to another centrifugation under the same conditions so as to complete the removal of vascular debris, of nuclei and of large myelinic fragments. A final centrifugation of the supernatant at 20,000 g, for 20 minutes, makes it possible to obtain a pellet enriched in mitochondria.

The pellet is taken up in 100 mM (mono- and dipotassium) phosphate buffer, pH 7.4, at the rate of 4 ml of buffer per gram of fresh tissue.

The enzymatic preparation thus obtained is fractionated into tubes at the rate of 0.5 ml of solution per tube and stored at −80° C. A storage of a duration of a few months does not cause any loss of activity.
b) Assay of the monoamine oxidase (MAO) activity
  * Principle of the measurement of the MAO enzymatic activity in vitro Serotonin (5HT) and β-phenylethylamine (β-PEA), which constitute the substrates specific for MAO A and MAO B respectively, are used to measure each activity. These molecules are labeled on their side chain with $^{14}$carbon and are converted by the MAOs, by oxidative deamination, to 5-hydroxyindoleacetaldehyde and to β-phenylacetaldehyde respectively, according to the scheme below:

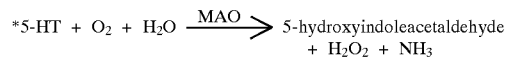
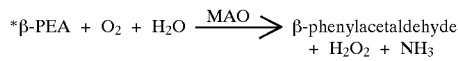

The mitochondria are incubated in the presence of one of the two radioactive substrates. After a defined time, the enzymatic reaction is stopped by precipitation of the mitochondrial proteins. The radioactive products are then extracted with a mixture of organic solvents. The MAO activity is then determined by counting the radioactivity of the products of the reaction.
  * Method of assay The standard assay is performed with:
  90 μl of 100 mM mono- and dipotassium phosphate buffer, of pH 7.4,
  50 ml of mitochondrial suspension,
  20 μl of H$_2$O/DMSO mixture corresponding to the dilution of the product to be tested in the case of the control or 20 μl of a solution of inhibitor to be tested at the chosen concentration,
  40 μl of radioactive substrate with a radioactivity equal to 0.05 μCI, for a final volume of 200 μl.

The reaction necessary for the assay is performed either after a preincubation of the enzyme (MAO A or MAO B) with the inhibitor to be tested, for a period of 30 minutes on a bath thermostated at 37° C., or without preincubation. In any case, the reaction is initiated by the addition of 40 μl of a 10$^{-5}$ molar solution of $^{14}$carbon-labeled 5-HT (of radioactive concentration=1.25 μCI/ml) or of a 5×10$^{-6}$ molar solution of $^{14}$carbon-labeled β-PEA (of radioactive concentration=1.25 μCI/ml).

The incubation of the reaction mixture is maintained for 60 minutes for 5-HT and 10 minutes for β-PEA, at the end of which the reaction is stopped by precipitation of the proteins by adding 200 ml of cold 4N HCl, and by immediately stirring the mixture obtained by means of a vortex for 5 seconds.

The extraction of the products of the reaction is performed by the addition of 1 ml of a mixture of toluene and ethyl acetate (1/1) followed by stirring on a vortex for 30 seconds and by centrifugation at 3000 revolutions/minute for 5 minutes. 500 μl of supernatant are collected and counted in 2 ml of toluene containing 0.4% diphenyloxazole by means of a Rackseta 1290 whose yield is 94%.

The reaction blank consists in carrying out the procedure in the same manner as for the standard test, but the substrate is added after precipitation of the mitochondrial proteins.
  * Kinetic conditions for the assay The enzymatic reactions are studied under the following conditions:
  the concentration of the enzyme is substantially less than that of the substrates,
  only the initial phase of the reaction is monitored.

These two conditions together set the framework of an enzymatic kinetic method at the stationary phase of the reaction.

The residual activity of the enzyme is determined by the following formula:

$$\frac{(cpm \text{ in the presence of the inhibitor} - cpm \text{ for the blank})}{(cpm \text{ for the control} - cpm \text{ for the blank})} \times 100$$

* Determination of the protein concentration of the mitochondrial suspension

It is performed with the aid of the assay kit Protein Assay Reagent from the company PIERCE CHEMICAL Co.

The optical density, read at the wavelength of 550 nm, is proportional to the protein concentration of a biological sample.

The protein concentration of the mitochondrial suspension is determined by comparison with a calibration series for bovine serum albumin diluted in the mitochondria-suspending buffer.

FIG. 1 presents this calibration series, with, on the y-axis, the optical density measured at 550 nm (OD 550 nm) and, on the x-axis, the bovine serum albumin (BSA) concentration expressed in mg/ml.

The mitochondrial suspension has an optical density equal to 0.238 at a 1/15th dilution, and equal to 0.124 at a 1/30th dilution. The protein concentration is therefore 6 mg/ml. It is adjusted, by dilution, to a working concentration of 0.6 mg/ml.
B/ Results:

The ICSO values for the inhibitors tested toward MAO A and MAO B, which represent the inhibitory concentrations capable of obtaining a 50% inhibition of these enzymes, are determined graphically from the curves of percentage residual activity of the MAOs for various concentrations of inhibitors.

Figure 2B:
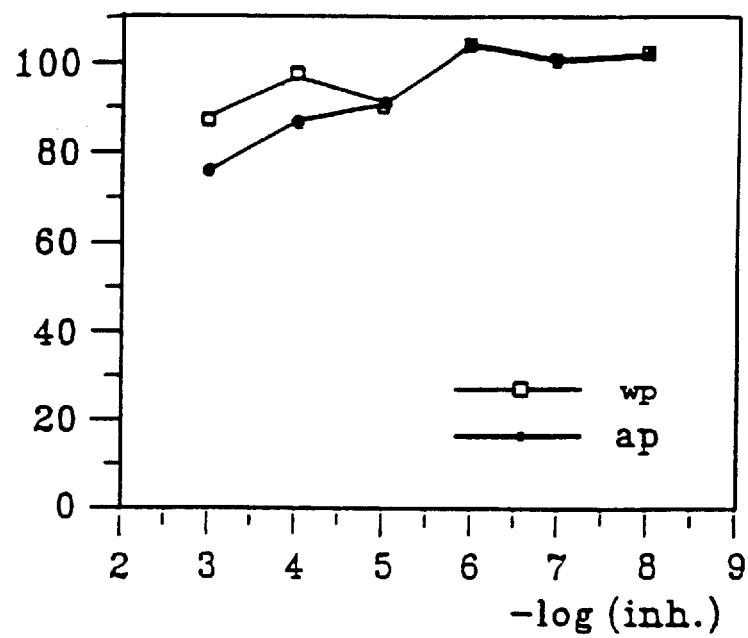
FIG. 2 illustrates the inhibitory activity of the compound (I-a2) toward MAO A and MAO B.
Figure 2B:
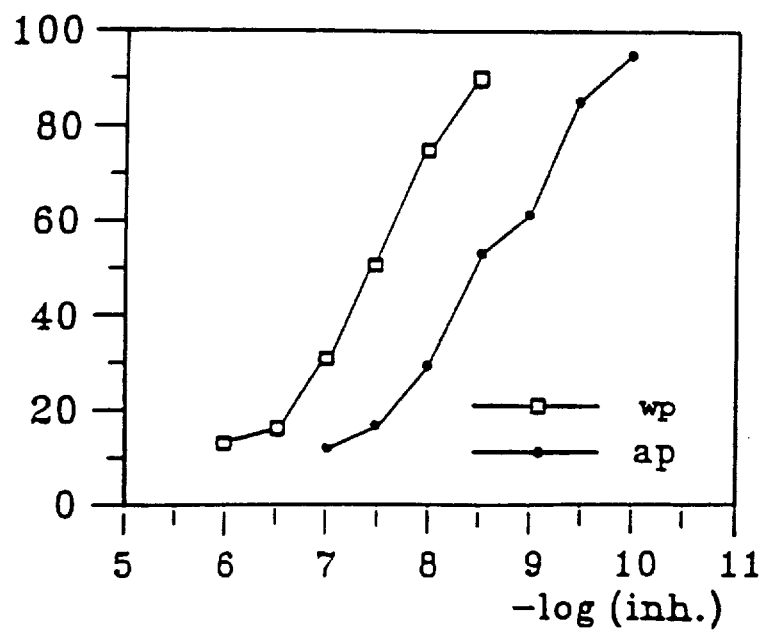
Figure 3A:
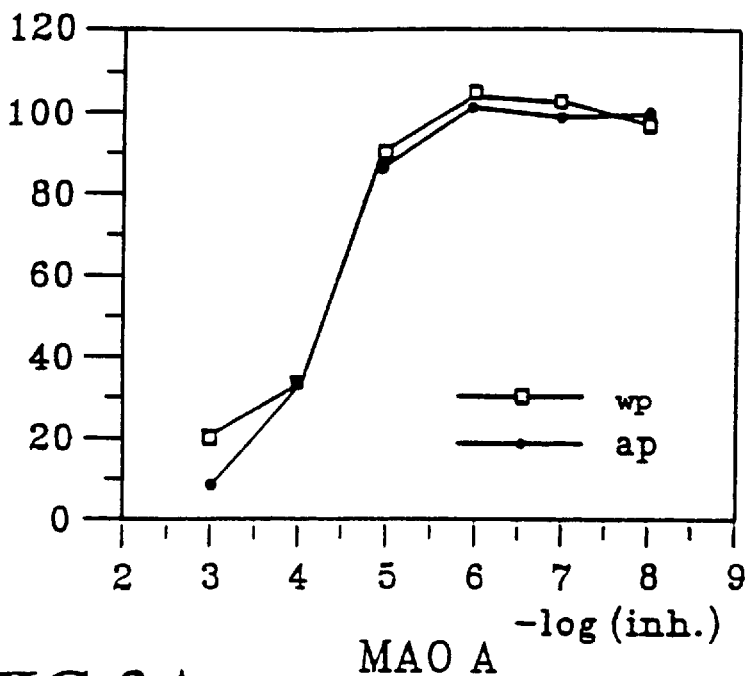
FIG. 3 illustrates the inhibitory activity of the compound (I-a4) toward MAO A and MAO B.
Figure 3B:
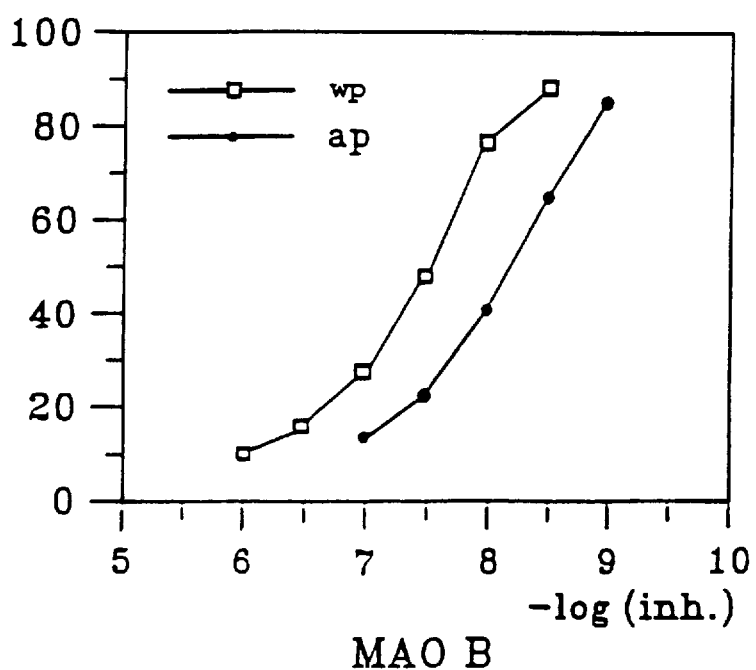

FIGS. 2 and 3 show, by way of examples, the curves of percentage residual activity of MAO A and MAO B obtained with the compounds (I-a2) and (I-a4) respectively, on the one hand without preincubation of the enzyme and the compound (wp), on the other hand after preincubation of the enzyme and the inhibitor (ap). The percentage of residual enzymatic activity is expressed on the y-axis and the logarithm in base 10 of the concentration of inhibitor is expressed on the x-axis.

Table 2 presents the $IC_{50}$ values, expressed in moles/liter, toward MAO A and toward MAO B, of various compounds of formula (I), which values are obtained, on the one hand, without preincubation of the enzyme and the compound and, on the other hand, with preincubation of the enzyme and the inhibitor.

TABLE 2

| Code No. | | $IC_{50}$ MAO A (M) | $IC_{50}$ MAO B (M) |
|---|---|---|---|
| I-a2 | wp | nd | $3.5 \times 10^{-8}$ |
| | ap | nd | $3 \times 10^{-9}$ |
| I-a2.1 | wp | nd | $4.3 \times 10^{-5}$ |
| | ap | nd | $6.9 \times 10^{-7}$ |
| I-a2.2 | wp | nd | $3 \times 10^{-6}$ |
| | ap | nd | $1.4 \times 10^{-6}$ |
| I-a2.3 | wp | nd | $1.13 \times 10^{-5}$ |
| 22 | ap | nd | $2.45 \times 10^{-7}$ |
| I-a2.4 | wp | nd | $2.8 \times 10^{-5}$ |
| | ap | nd | $2.15 \times 10^{-6}$ |
| I-a2.5 | wp | nd | precipitate |
| | ap | nd | $3.8 \times 10^{-7}$ |
| I-a4 | wp | $5 \times 10^{-5}$ | $2.8 \times 10^{-8}$ |
| | ap | $5 \times 10^{-5}$ | $6.3 \times 10^{-9}$ |
| I-a6 | wp | $5.3 \times 10^{-5}$ | $3 \times 10^{-6}$ |
| | ap | $6.8 \times 10^{-6}$ | $1.5 \times 10^{-8}$ |
| I-a10 | wp | nd | $4.1 \times 10^{-6}$ |
| | ap | nd | $3.6 \times 10^{-7}$ |
| I-b2 | wp | nd | $2.2 \times 10^{-5}$ |
| | ap | nd | $6.3 \times 10^{-6}$ |
| I-b4 | wp | nd | $3.5 \times 10^{-5}$ |
| | ap | nd | $10^{-5}$ |
| I-c1 | wp | nd | $2.8 \times 10^{-4}$ |
| | ap | nd | $1.2 \times 10^{-4}$ |
| I-c2 | wp | nd | $1.8 \times 10^{-6}$ |
| | ap | nd | $2.5 \times 10^{-6}$ | wp: without preincubation
ap: after preincubation
nd: not determinable, excessively weak inhibition 21.2 Reversibility of the inhibitory activity toward the MAO BEs The reversibility of the inhibitory activity of the compounds of formula (I) is determined by comparing the percentages of residual activity of monoamine oxidase B, which are obtained before and after washing a mixture of enzyme and inhibitor previously subjected to incubation for a period of 30 minutes at 37° C.

A/ Principle:

The enzyme, in solution in phosphate buffer, and the inhibitor are incubated for 30 minutes at 37° C. At the end of this incubation, a proportion of the solution is subjected to a test of activity as described below, which makes it possible to determine the percentages of enzymatic activity before washing of the enzyme+inhibitor solution. The rest of the solution is diluted 10-fold with phosphate buffer and then centrifuged for 20 minutes at 27,000 g in a refrigerated centrifuge. The supernatants are removed. The pellets are taken up in a volume of phosphate buffer corresponding to the quantity of supernatant removed. Centrifugation is performed under the same conditions as above. The supernatants are removed. The pellets are again taken up in a volume of phosphate buffer equal to the volume of supernatant removed. Centrifugation is again performed and the pellets are taken up in the minimum quantity of phosphate buffer necessary for the activity test, which makes it possible to define the percentages of enzymatic activity after washing the enzyme+inhibitor solution.

Deprenyl, an irreversible inhibitor of MAO B, serves as reference product.

A control is prepared using 1% DMSO (dimethyl sulfoxide) in place of the inhibitor.

B/ Test of activity:

Each test is performed with:

160 $\mu$l of solution containing MAO B and the inhibitor or DMSO in phosphate buffer, 40 $\mu$l of a 5 $\mu$M solution of $^{14}$carbon-labeled β-phenylethylamine (radioactivity=0.25 $\mu$Ci).

The reaction is initiated by adding the 40 $\mu$l of β-phenylethylamine. The reaction time is one minute. The reaction is stopped by addition of 200 $\mu$l of 4N HCl and then 1 ml of a mixture of ethyl acetate and toluene (1/1) is added in order to extract the radioactive product. The tubes are centrifuged for 5 minutes at 3000 revolutions per minute in a refrigerated centrifuge. 2 ml of scintillant are added to 500 $\mu$l of supernatant directly in the tubes. The counting is performed over 120 seconds.

C/ Results:

Table 3 presents the mean percentages of residual MAO activity which are obtained from 4 assays, for the compound (I-a2) and deprenyl, before and after washing the enzyme+inhibitor mixture.

TABLE 3

| | Percentage of residual MAO activity | |
|---|---|---|
| Inhibitor | Before washing | After washing |
| Compound (I-a2) | 14 | 105 |
| Deprenyl | 25.6% | 14.7% |

Figure 4:
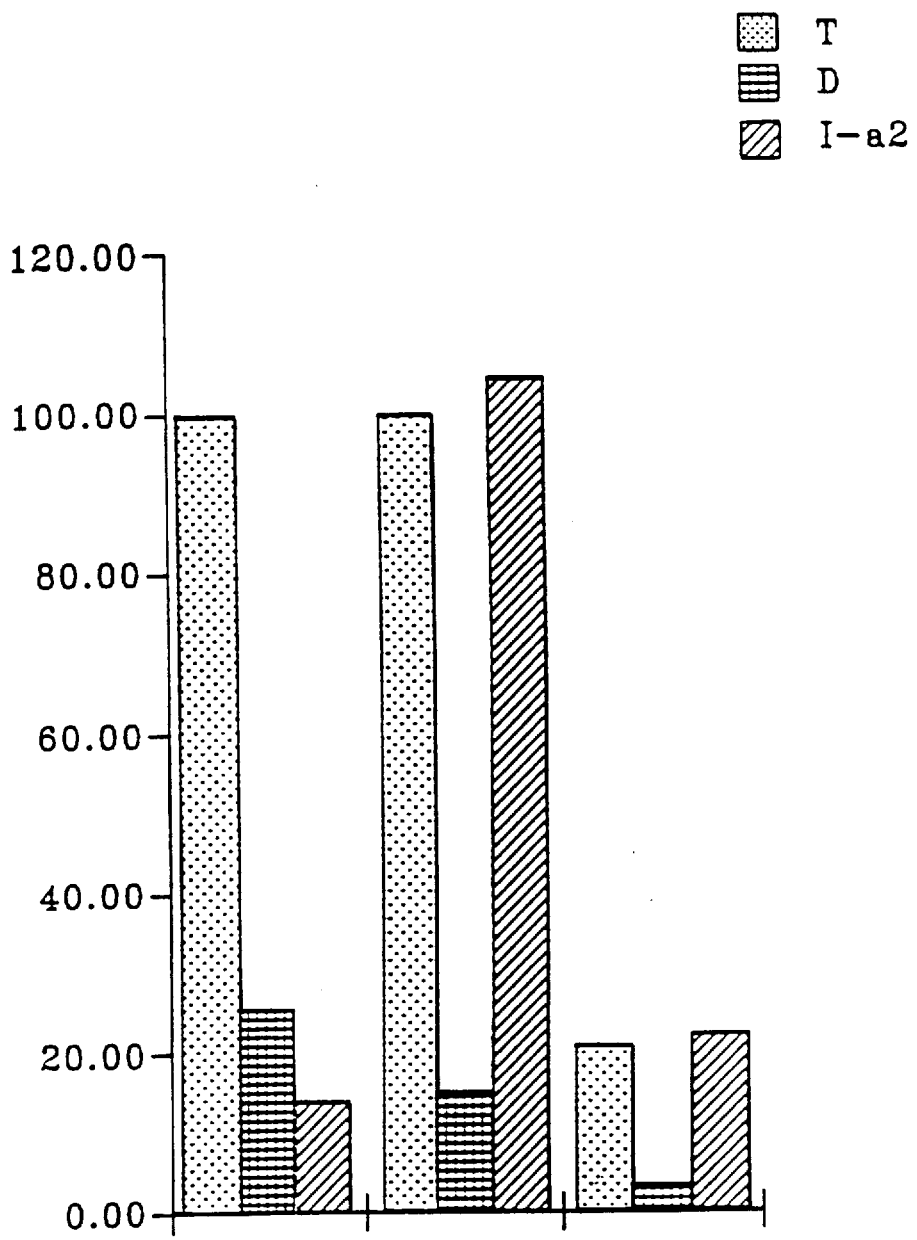
FIG. 4 illustrates, in the form of histograms, the reversibility of the inhibitory activity of the compound (I-a2) toward MAO B.

FIG. 4 shows, in the form of three histograms, the results of Table 3 as well as the loss of enzymatic activity linked to time. The percentage of residual enzymatic activity is expressed on the y-axis.

The first histogram corresponds to the mean percentages of residual MAO activity which are obtained with the control (C), deprenyl (D) and the compound (I-a2), respectively, before washing the mixture. The second histogram corresponds to the mean percentages of residual MAO activity which are obtained with the control (C), deprenyl (D) and the compound (I-a2), respectively, after washing the mixture. The third histogram shows, for the control and the inhibitors tested, the loss of enzymatic activity linked to time.

21.3 Toxicity

The evaluation of the cytotoxicity of the compounds of formula (I) was the subject of two different tests:

an MTT test (3-[4,5-dimethylthiazol-2-yl]-2,5-diphenyltetrazolium bromide) on adherent cells, a test on the cells in suspension.

A/ KTT test on adherent calls:

Epithelial cells, Hela Ohio, are used. This cell line is derived from a human cervical cancer. The cells are cultured in EMEM medium supplemented with 10% fetal calf serum.

The compounds in accordance with the invention are tested at concentrations of between $10^{-4}$ and $10^{-8}$ molar in 75% DMSO.

In a 96-well plate, $3 \times 10^4$ Bela cells in 100 µl of culture medium are deposited per well. The plates are incubated for 18 hours, at a temperature of 37° C., in a humid atmosphere with 5% $CO_2$. The cells can thus adhere to their support. A solution of compound to be tested, with a concentration of between $10^{-4}$ and $10^{-8}$ molar or a 75% solution of DMSO intended to obtain growth controls, is added to the wells.

After incubating for a period of 24 hours, in a humid atmosphere, with 5% $CO_2$, the cells are washed with PBS. 10 µl of a solution containing 5 mg/ml of MTT in PBS are then added with 100 µl of medium to each well. The plates are incubated for 4 hours at 37° C. in a humid atmosphere and with 5% $CO_2$. MTT is metabolized in the live cells to an insoluble purple compound. At the end of the incubation, the wells are washed with PBS in order to remove the MTT in suspension. 100 µl of DMSO, added to the wells, cause lysis of the cells and the solubilization of the colored product. The plates are stirred for 15 minutes in order to homogenize the medium and the suspension of purple product. The concentration of the metabolite in the wells is read by photometry at a wavelength of 550 nm and the number of live cells is a function of the optical density obtained. The viability index is calculated thus:

$$\text{Viability index} = 1 - \frac{OD_t - OD}{OD_t}$$

$OD_t$ being the optical density obtained for cells treated with DMSO and OD being the optical density for the cells treated with a compound in accordance with the invention.
B/ Test performed on the cells in suspension:

Daudi cells are used. This cell line is derived from a human Burkitt's lymphoma. The cells are cultured in an RPMI medium supplemented with 10% fetal calf serum.

The compounds in accordance with the invention are used at concentrations of between $10^{-4}$ and $10^{-8}$ molar in 75% DMSO.

Each well of a 24-well plate is inoculated with 100 µl of a cell suspension containing $2 \times 10^5$ cells per ml. Each well receives a compound to be tested, at a concentration of between $10^{-4}$ and $10^{-8}$ molar or 75% DMSO (growth controls).

The plates are incubated for 24 hours at 37° C., in a humid atmosphere and with 5% $CO_2$. After homogenization of the medium, 100 ml of suspension are collected from the well and mixed with 100 ml of Trypan blue at 0.04% in PBS. The Trypan blue diffuses in the dead cells but not in the live cells.

The live (refringent) and dead (blue) cells are counted on a Malassez cell. The live cell fraction (Lf) is equal to the ratio of the number of live cells to the total number of cells. The viability index is equal to:

$$Lf = \frac{\text{live cells}}{\text{live and dead cells}}$$

$$\text{Viability index} = 1 - \frac{Lft - Lf}{Lft}$$

Lft being the live fraction of the cells treated with DMSO and Lf being the live fraction of cells treated with the compounds in accordance with the invention.
C/ Results:

Table 4 below presents the results of the cytotoxicity tests performed with compounds of formula (I). Two values were retained for each type of test:

* the lethal dose (50 LD50) corresponding to the concentration, expressed in moles/liter, of compound for which 50% of the cells are killed.

* the maximum concentration of compound (MC100), expressed in moles/liter, for which all the cells are alive.

TABLE 4

| Code | MTT test on adherent cells | | Test on cells in suspension | |
|---|---|---|---|---|
| No. | LD50 (M) | MC100 (M) | LD50 (M) | MC100 (M) |
| I-a2 | $10^{-4}$ | $10^{-5}$ | $10^{-4}$ | $10^{-5}$ |
| I-a2.2 | $3 \times 10^{-5}$ | $6.5 \times 10^{-7}$ | $2.2 \times 10^{-5}$ | $10^{-5}$ |
| I-a2.3 | $2.2 \times 10^5$ | $6 \times 10^{-7}$ | $5 \times 10^{-5}$ | $10^{-5}$ |
| I-a2.4 | $4 \times 10^{-5}$ | $2.3 \times 10^{-6}$ | $6.5 \times 10^{-5}$ | $1.25 \times 10^{-5}$ |
| I-a4 | $10^{-4}$ | $10^{-5}$ | $10^{-4}$ | $10^{-5}$ |

We claim:

1. A method of selectively inhibiting monoamine oxidase B activity in a human or an animal, which method comprises administering to said human or said animal an effective amount of a compound of formula (I):

$$R_1-\text{C}_6H_4-\underset{R_2}{\underset{|}{C}}=N-\underset{\underset{[N(H)_y]_n}{\underset{|}{C=O}}}{\underset{|}{N}}-(CH_2)_p-R_3 \quad (I)$$

in which:
R$_1$ represents a hydrogen atom, a benzyloxy group or a phenylethoxy group whose phenyl ring is optionally substituted;

p is an integer from 0 to 3;

R$_3$ represents a hydrogen atom, a CN group, a hydroxyl group, a CCH group, a ($C_1$–$C_3$ alkoxy) carbonyl group or a $C_1$–$C_3$ alkylated cyanomethyl group;

R$_2$ represents a hydrogen atom or a $C_1$–$C_3$ alkyl group;

n is equal to 0 or 1, in which case:
if n=0, R$_4$ represents a $C_1$–$C_3$ alkyl group or a $C_1$–$C_3$ alkoxy group; whereas
if n=1, y=1 and R$_4$ represents a $C_1$–$C_3$ alkyl group, a $C_1$–$C_3$ alkoxy group or a phenyl group.

2. The method as claimed in claim 1, wherein R$_1$ represents a benzyloxy group whose phenyl ring is optionally substituted with one or more halogen atoms and/or one or more NO$_2$ groups and/or one or more $C_1$–$C_3$ alkyl groups and/or one or more $C_1$–$C_3$ alkoxy groups.

3. The method as claimed in claim 1 or claim 2, wherein the compound is selected from the group consisting of:
4-(benzyloxy)benzaldehyde acetyl(2-cyanoethyl) hydrazone,
4-[(4-methylbenzyl)oxy]benzaldehyde acetyl (2-cyanoethyl)hydrazone [(I-a2.1)],
4-[(4-nitrobenzyl)oxy]benzaldehyde acetyl(2-cyanoethyl)hydrazone [(I-a2.2)],
4-[(4-chlorobenzyl)oxy]benzaldehyde acetyl(2-cyanoathyl)hydrazone [(I-a2.3)],
4-[(4-methoxybenzyl)oxy]benzaldehyde acetyl(2-cyanoethyl)hydrazone [(I-a2.4)],
4-[(2,4-ditlalorobenzyl)oxy]benzaldehyde acetyl(2-cyanoethyl)hydrazone [(I-a2.5)],
4-[2-chlorobenzyl)oxy]benzaldehyde acetyl (2-cyanoethyl)hydrazone [(I a2.6)],
4-(benzyloxy)benzaldehyde acetyl(2-hydroxyethyl) hydrazone [(I-a4)],
4-(benzyloxy)benzaldehyde acetyl (2-methoxycarbonylethyl)hydrazone (I-a5], 4-(2-phenylethoxy)benzaldehyde acetyl(2-cyanoethyl) hydrazone [(I-a6)], 4-(benzyloxy)benzaldehyde acetyl (2-cyanopropyl) hydrazone [(I-a7)], 4-(benzyloxy)benzaldehyde acetyl(cyanomethyl) hydrazone [(I-a8)], 4-(benzyloxy)benzaldehyde acetyl (3-cyanopropyl) hydrazone [(I-a9)], 4-(benzyloxy)benzaldehyde acetylpropargylhydrazone [(I-a10)], 4 (benzyloxy) benzaldehyde(2-cyanoethyl) (ethoxycarbonyl)hydrazone [(I-b2)], 4-(benzyloxy)benzaldehyde(2-hydroxyethyl) (ethoxycarbonyl)hydrazone [(I-b4)], benzaldehyde(2-cyanoethyl) (N-methylcarbamoyl) hydrazone [(I-c1)], 4-(benzyloxy)benzaldehyde(2-cyanoethyl) (N-methylcarbamoyl)hydrazone [(I-c2)], benzaldehyde(2-cyanoethyl) (N-phenylcarbamoyl) hydrazone [(I-d1)], 4-(benzyloxy)benzaldehyde(2-cyanoethyl) (N-phenylcarbamoyl)hydrazone [(T-d2)], and 4-(benzyloxy)acetophenone acetyl (2-cyanoethyl) hydrazone [(I-e1)].

4. A compound selected from the group consisting of compounds having the following specific formulae:

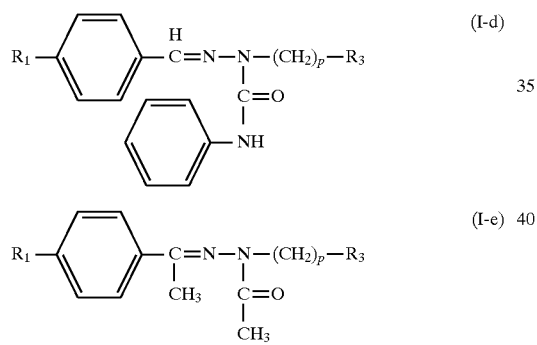

in which:

$R_1$ represents a hydrogen atom, a benzyloxy group or a phenylethoxy group whose phenyl ring is optionally substituted, provided that $R_1$ is different from a hydrogen atom in the specific formula (I-e);

p is an integer from 0 to 3; and $R_3$ represents a CN group, an OH group, a CCH group, a ($C_1$–$C_3$ alkoxy) carbonyl group or a $C_1$-$C_3$ alkylated cyanomethyl group.

5. The compound as claimed in claim 4, selected from the group consisting of:

benzaldehyde(2-cyanoethyl) (N-phenylcarbamoyl) hydrazone [(I-d1)], 4-(benzyloxy)benzaldehyde(2-cyanoethyl) (N-phenylcarbamoyl)hydrazone [(I d2)], and 4-(benzyloxy)acetophenone acetyl (2-cyanoethyl) hydrazone [(I-e1)].

6. A process for the preparation of a compound of formula (I-d)

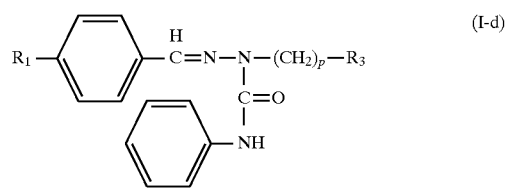

which comprises: reacting an aromatic aldehyde of formula:

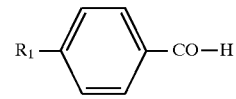

in which:

$R_1$ represents a hydrogen atom, a benzyloxy or phenylethoxy group whose phenyl ring is optionally substituted, and a hydrazine of formula: $NH_2$—NH—$(CH_2)_p$—$R_3$ in which:

p is an integer from 0 to 3;

$R_3$ represents a CN group, an OH group, a CCH group, a ($C_1$—$C_3$ alkoxy)carbonyl group or a $C_1$—$C_3$ alkylated cyanomethyl group to form a condensation product; and acylating the condensation product to form a compound of formula (I-d).

7. A process for the preparation of a compound of specific formula (I-e)

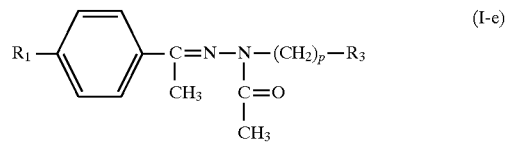

which comprises:

reacting an aromatic aldehyde of formula:

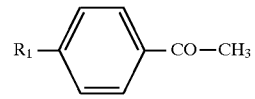

in which:

$R_1$ represents a benzyloxy or phenylethoxy group whose phenyl ring is optionally substituted; and:

a hydrazine of formula: $NH_2$—NH—$(CH_2)_p$—$R_3$ in which:

p is an integer from 0 to 3;

$R_3$ represents a CN group, an OH group, a CCH group, a ($C_1$—$C_3$ alkoxy)carbonyl group or a $C_1$—$C_3$ alkylated cyanomethyl group;

or a hydrazine of formula: $NH_2$—NH—CO—$CH_3$ to form a condensation product; and acylating the condensation product or alkylating the condensation product using a reagent of formula: Hal—$(CH_2)_p$—C≡Z in which:

p is an integer from 0 to 3;

Hal represents a halogen atom;

Z represents a CH group or a nitrogen atom, or by a reagent of formula: Br—$(CH_2)_p$—COO—($C_1$-$C_3$ alkyl) in which p is an integer from 0 to 3 to form a compound of formula (I-e).

8. The method as claimed in claim 3, wherein the compound is 4(benzyloxy)-benzaldehyde acetyl(2-cyanoethyl) hydrazone [(I-a2)].

9. The method as claimed in claim 3, wherein the compound is benzaldehyde (2-cyanoethyl(N-phenyl-carbamoyl)hydrazone [(I-d1)].

10. The method as claimed in claim 3, wherein the compound is 4-(benzyloxy)benzaldehyde (2-cyanoethyl)-(N-phenylcarbamoyl)hydrazone [(I -d2)].

11. The method as claimed in claim 3, wherein the compound is 4-(benzyloxy)acetophenone acetyl(2-cyanoethyl)hydrazone [(I-31)].

12. The method as claimed in claim 6, wherein said step of acylating the condensation product comprises acylating the condensation product using phenyl isocyanate.

13. The method as claimed in claim 7, wherein said step of acylating the condensation product comprises acylating the condensation product using an acid chloride.

\* \* \* \* \*

UNITED STATES PATENT AND TRADEMARK OFFICE
CERTIFICATE OF CORRECTION

PATENT NO. : 5,811,456
DATED : September 22, 1998
INVENTOR(S) : Seman et al.

It is certified that error appears in the above-identified patent and that said Letters Patent is hereby corrected as shown below:

On the title page: Item [56]

In the References Cited, U.S. PATENT DOCUMENTS, line 3, "Cauro" should read --Catino--; FOREIGN PATENT DOCUMENTS, add --428421 5/1991 European Pat. Off. .--; OTHER PUBLICATIONS, line 20, "dohydrouracil" should read --dihydrouracil--.

Column 18, lines 52, 54, 56, 58, "hydrazonc" should read --hydrazone--; line 56, "cyanoathyl" should read --cyanoethyl--; line 59, "ditlalorobenzyl" should read --dichlorobenzyl--; line 61, "acctyl" should read --acetyl--.

Column 19, line 1 "phenylcthoxy" should read --phenylethoxy--; line 22, "(T-d2)" should read --(I-d2)--.

Column 21, line 9, "(I-31)" should read --(I-e1)--.

Signed and Sealed this

Twenty-seventh Day of April, 1999

Attest:

Q. TODD DICKINSON

*Attesting Officer*  *Acting Commissioner of Patents and Trademarks*